(12) United States Patent  
Loda

(10) Patent No.: US 12,303,416 B2  
(45) Date of Patent: May 20, 2025

(54) WEARABLE TUBULAR TEXTILE ARTICLE

(71) Applicant: PUNTO AZZURRO S.R.L., Rovetta (IT)

(72) Inventor: Roberto Loda, Onore (IT)

(73) Assignee: PUNTO AZZURRO S.R. L., Rovetta (IT)

( * ) Notice: Subject to any disclaimer, the term of this patent is extended or adjusted under 35 U.S.C. 154(b) by 570 days.

(21) Appl. No.: 17/612,341

(22) PCT Filed: Apr. 22, 2020

(86) PCT No.: PCT/IB2020/053806  
§ 371 (c)(1),  
(2) Date: Nov. 18, 2021

(87) PCT Pub. No.: WO2020/234664  
PCT Pub. Date: Nov. 26, 2020

(65) Prior Publication Data  
US 2022/0241101 A1 Aug. 4, 2022

(30) Foreign Application Priority Data  
May 21, 2019 (IT) .......................... 102019000007051

(51) Int. Cl.  
*A61F 5/01* (2006.01)  
*A41D 27/24* (2006.01)

(52) U.S. Cl.  
CPC .......... *A61F 5/0109* (2013.01); *A41D 27/245* (2013.01); *A61F 5/0123* (2013.01); *A41D 2300/52* (2013.01); *A41D 2400/32* (2013.01)

(58) Field of Classification Search  
CPC .... A61F 5/0109; A61F 5/0123; A61F 5/0125; A61F 5/01; A61F 5/00; A61F 5/0104;

(Continued)

(56) References Cited

U.S. PATENT DOCUMENTS 663,749 A * 12/1900 Gorse ..................... A61F 13/00  
473/214  
6,592,539 B1 * 7/2003 Einarsson ............. A61F 5/0109  
623/32

(Continued)

FOREIGN PATENT DOCUMENTS

CN 102548438 A 7/2012  
EP 0639361 A1 2/1995

(Continued)

OTHER PUBLICATIONS

Translation of FR-2873545-A1 (Year: 2006).*

(Continued)

*Primary Examiner* — Keri J Nelson  
*Assistant Examiner* — Daniel A Miller  
(74) *Attorney, Agent, or Firm* — Ferguson Case Orr Paterson

(57) ABSTRACT

A wearable textile article has a tubular element having an external side and an internal side, a first and a second reinforcement bands placed along a direction extending from a lower opening to an upper opening of the tubular element. A first and a second fabric portions made of fabric obtained from weaving weft threads and warp threads of polymeric material are fused together along a first and a second fusing areas. The first reinforcement band at least partially overlaps the first fusing area and the second reinforcement band at least partially overlaps the second fusing area. A method for manufacturing the wearable textile article includes fusing together the first and second fabric portions along the first and second fusing areas to obtain the tubular element, and joining the first and second reinforcement bands in a partially overlapping way with respect to the first and second fusing areas on the external or internal side.

13 Claims, 8 Drawing Sheets

(58) Field of Classification Search
CPC ...... A61F 13/00; A61F 13/101; A61F 13/061;
A61F 13/00017; A61F 13/00029; A61F
13/00038; A61F 13/08; A61F 2013/0028;
A61F 2005/0176; A41D 27/245; A41D
27/24; A41D 2300/52; A41D 2400/32;
A41D 13/00; A41D 17/02; A41D 27/10;
A41D 13/065; A41B 7/12
USPC .......................................................... 602/5
See application file for complete search history.

(56) References Cited

U.S. PATENT DOCUMENTS

| | | | |
|---|---|---|---|
| 2003/0083605 | A1 | 5/2003 | Edmund |
| 2008/0139982 | A1* | 6/2008 | Magnusson ............ A61F 13/101 |
| | | | 602/5 |
| 2016/0081835 | A1* | 3/2016 | Grange ................. A61F 13/061 |
| | | | 602/5 |
| 2018/0042754 | A1 | 2/2018 | Ingimundarson |
| 2018/0104108 | A1* | 4/2018 | Carpinelli ............. A61F 13/101 |
| 2019/0308028 | A1* | 10/2019 | White ..................... A61N 2/02 |

FOREIGN PATENT DOCUMENTS

| | | | |
|---|---|---|---|
| FR | 2873545 A1 * | 2/2006 | ........... A41D 27/245 |
| GB | 2241647 A | 9/1991 | |
| JP | H04-057904 | 2/1992 | |
| JP | 2003227014 | 8/2003 | |
| JP | 2009041152 | 2/2009 | |
| JP | 2016069764 | 5/2016 | |
| WO | 0049982 A1 | 8/2000 | |
| WO | 2008077334 A1 | 7/2008 | |

OTHER PUBLICATIONS

European Patent Office, International Search Report issued in PCT/IB2020/053806, mailed Aug. 26, 2020, Rijswijk, NL.
International Written Opinion issued in PCT/IB2020/053806, mailed Aug. 26, 2020,.
Italian Search Report issued in 201900007051, mailed Jan. 22, 2020.
International Preliminary Report on Patentability issued in PCT/IB2020/053806, mailed Oct. 7, 2021.
International Preliminary Search Report issued in PCT/IB2020/053806, mailed Nov. 24, 2021.
Office Action issued in Chinese Application in 202080052253.7 issued Nov. 16, 2023.
Office Action issued in Japanese Application in 2021-569114 issued Nov. 27, 2023.

* cited by examiner

WEARABLE TUBULAR TEXTILE ARTICLE

CROSS-REFERENCE TO RELATED APPLICATIONS

This application is a National Phase Application of PCT International Application No. PCT/IB2020/053806, having an International Filing Date of Apr. 22, 2020 which claims the benefit of priority to Italian Patent Application No. 102019000007051, filed May 21, 2019, each of which is hereby incorporated by reference in its entirety.

FIELD OF THE INVENTION

The present invention refers to a wearable textile article, in particular a tubular textile article to be worn after a sports activity or, for example, during post-traumatic rehabilitation for muscle recovery.

BACKGROUND OF THE INVENTION

It is known that small muscle accidents may occur during physical exercise resulting in a need to support some body segments because they have been weakened and/or are in pain. At the same time, there is a need to prevent accidents by providing adequate support to the muscles in the body segments subjected to the greatest stresses during physical exercise.

To that end, in the field of wearable aids for sports activities or rehabilitation, there are known boots and braces made of elastic synthetic fabric (knee braces, calf braces, wrist braces, etc.) for supporting or warming up the muscle while performing motor activities.

However, these types of wearable aids are made by means of a knitted fabric, generally made with knitting or hosiery machines to obtain a tubular product. Knitted fabric inconveniently provides a different mechanical response depending on the direction of application of the drafting force. This leads to an inhomogeneous compression and support action on the body segment. In particular, the knitted fabric's response to traction in one direction involves greater deformation of the fabric compared to a direction perpendicular to that direction. This is due to the typical shape of the loops of fabric obtained with the knitting technique.

Furthermore, tubular knitted articles from the prior art have poor flexibility for the making of different sizes and do not make it possible to support the muscle/tendon system and ligaments in a homogeneous and effective way.

SUMMARY OF THE INVENTION

One of the purposes of this invention is to propose a wearable textile article capable of overcoming the drawbacks of the tubular products from the prior art. In particular, one of the purposes of this invention is to support the muscle in its natural repair and regeneration, and therefore to serve a purpose of preventing trauma. Another purpose of this invention is to allow for improved flexibility of use and improved flexibility and effectiveness in making the wearable textile article.

These purposes are achieved with a wearable textile article and with a method for making the wearable textile article in accordance with the enclosed independent claims. The dependent claims describe preferred or advantageous embodiments of the wearable textile article and of the method.

BRIEF DESCRIPTION OF THE DRAWINGS

The features and advantages of the wearable textile article and of the method for making the textile article according to the invention will become clear from the description given below of its preferred embodiments, given solely as a non-limiting example in reference to the enclosed figures, wherein.

DETAILED DESCRIPTION

Figure 1:
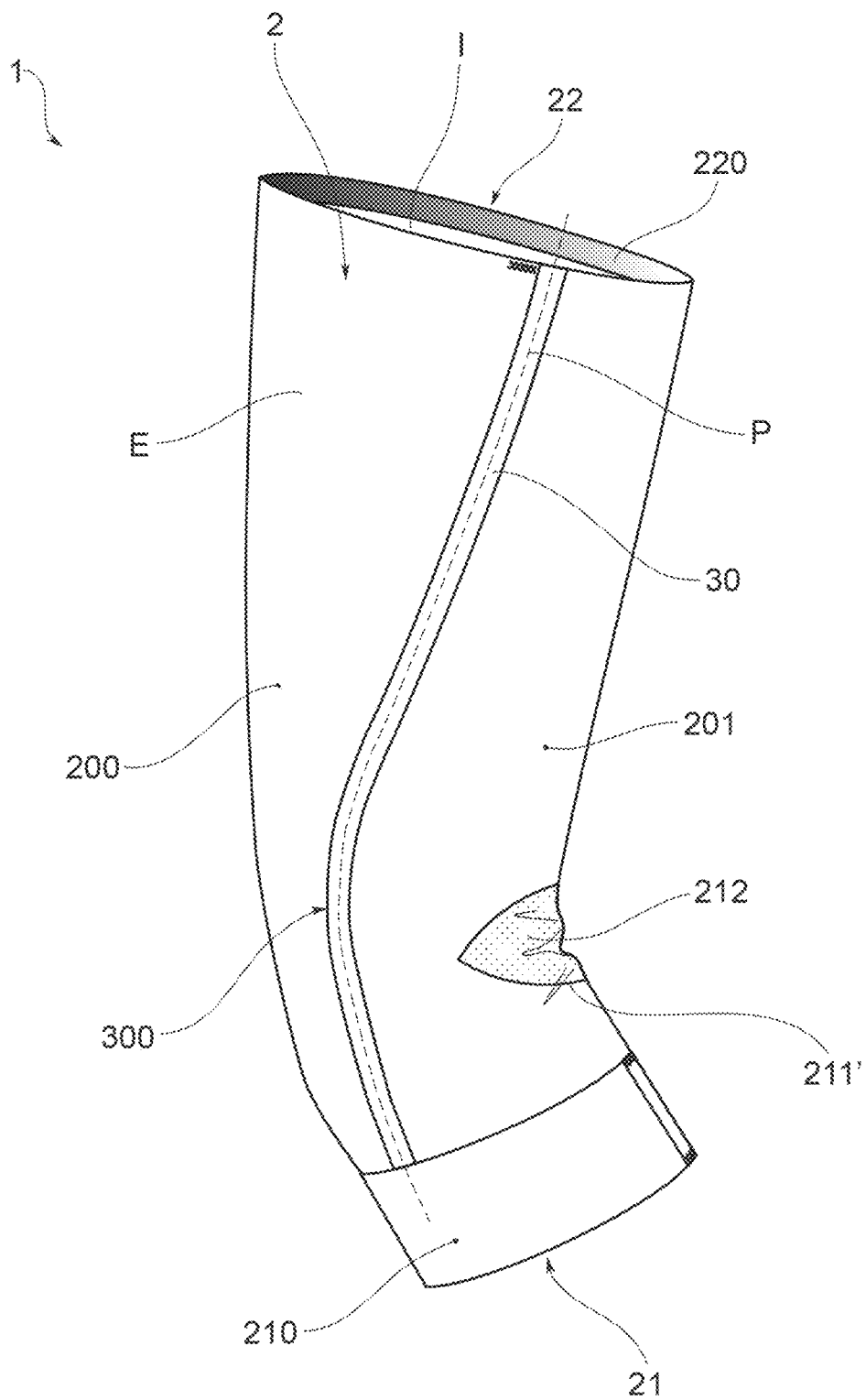
FIG. 1 shows a side view of the wearable textile article, according to one embodiment of the invention.
Figure 3:
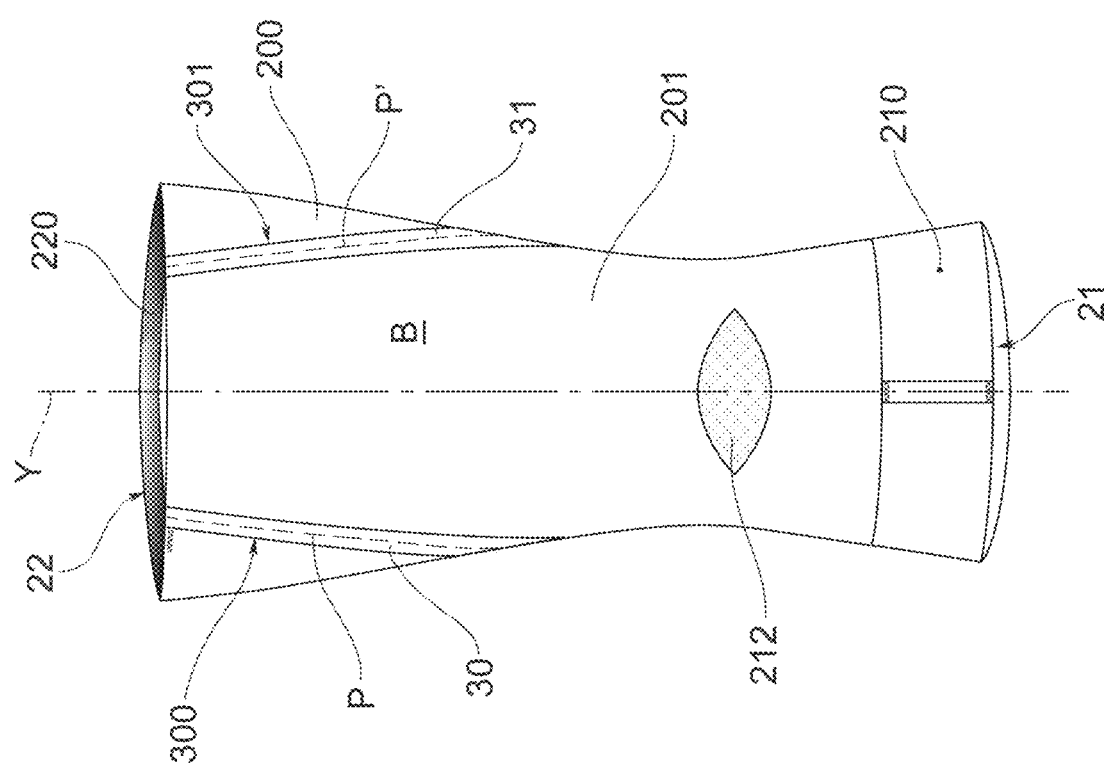
FIG. 3 shows a rear view of the wearable textile article of FIG. 1.
Figure 2:
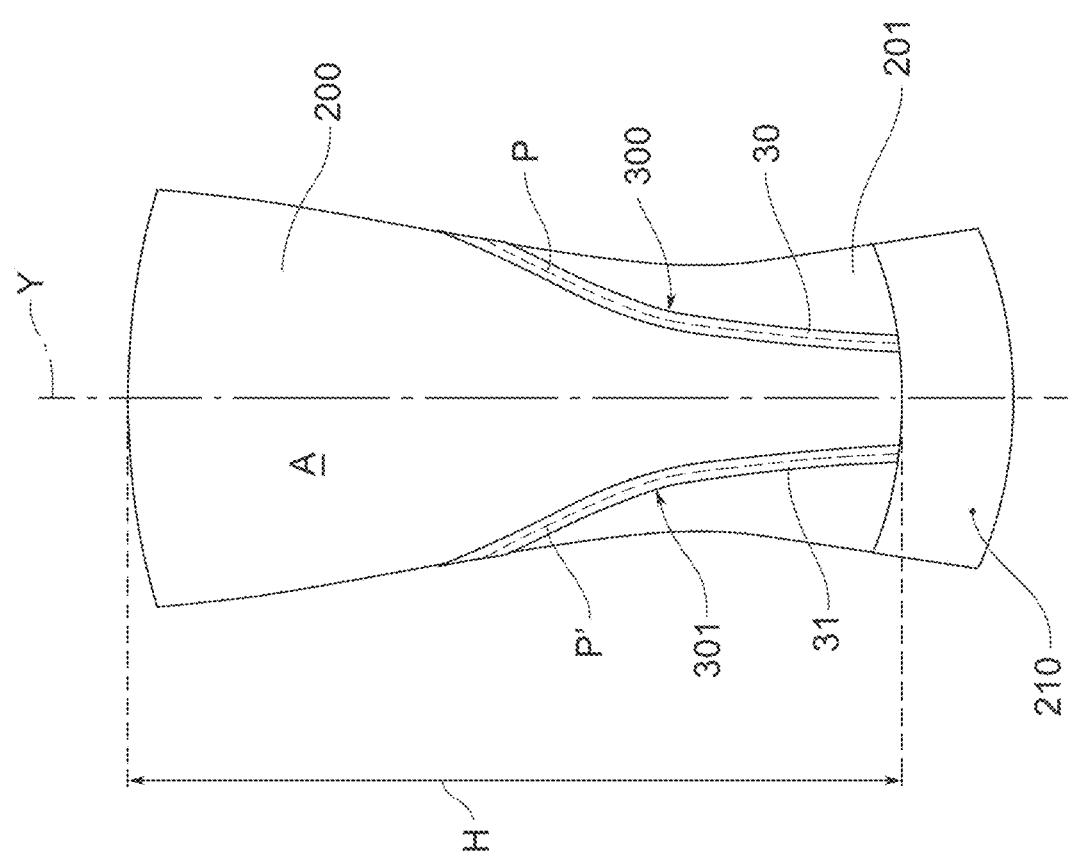
FIG. 2 shows a front view of the wearable textile article of FIG. 1.

In reference to the aforementioned figures, the number 1 refers to a wearable textile article for assisting with muscle function, particularly after engaging in motor activity. The wearable textile article is preferably a sleeve that can be worn on the limbs, such as a thigh brace or a calf brace or an ankle brace or a sleeve that can be worn on one of the upper limbs, around the elbow, such as an elbow brace or arm brace. The wearable textile article preferably has a length such that it simultaneously surrounds a body segment and a joint, so as to adequately support the muscles of the entire joint while performing the activity.

Wearable textile article 1 comprises a tubular element 2 having a lower opening 21 and an upper opening 22, in such a way that it is put on through said openings.

In particular, wearable textile article 1 comprises an internal side I suitable for coming into contact with a part of the human or animal body, and an external side E opposite internal side I and therefore facing the outside environment when textile article 1 is being worn.

Tubular element 2 comprises at least a first fabric portion 200 and a second fabric portion 201, each made of a fabric made by the weaving of weft threads and warp threads made of polymeric material, preferably a synthetic polymeric material, such as polyamide, polyester, elastane, and/or recycled fibers. In other words, each of these first and second fabric portions 200, 201 is not made by knitting or in a knitting machine, but instead is made by weaving weft threads and warp threads, for example on a loom.

In addition, tubular element 2 comprises a first fusing area 300 and a second fusing area 301 along which first fabric portion 200 is fused to second fabric portion 201, preferably by ultrasonic bonding or heat-sealing (with or without using an adhesive), so as to obtain a tubular shape completely free of stitching.

In particular, first fabric portion 200 and/or second fabric portion 201 preferably is/are a flat fabric portion.

According to one embodiment, a first reinforcement band 30 and a second reinforcement band 31 are applied to external side E of tubular element 2. Preferably, first reinforcement band 30 and second reinforcement band 31 are only applied to external side E.

According to an embodiment variant, a first reinforcement band 30 and a second reinforcement band 31 are applied to internal side I of tubular element 2. According to this variant, first reinforcement band 30 and second reinforcement band 31 are preferably only applied to internal side I.

According to yet another variant, first reinforcement band 30 and second reinforcement band 31 are applied to both internal side I and external side E.

According to the invention, each of these first and second reinforcement bands 30, 31 is placed along a path P, P' that lies primarily along a direction extending from lower opening 21 to upper opening 22, preferably a curved path P, P'.

In addition, first reinforcement band 30 at least partially overlaps first fusing area 300 and second reinforcement band 31 at least partially overlaps second fusing area 301.

Preferably and in particular, first reinforcement band 30 totally covers first fusing area 300 and second reinforcement band 31 totally covers second fusing area 301.

First and second reinforcement bands 30, 31 provide an additional support effect for tendon-muscle function and particularly an additional support effect for the muscles of the joint around which the wearable textile article is being worn. In particular, first and second reinforcement bands 30, 31 are arranged so as to be substantially parallel to and/or aligned with the direction of the primary muscles of the body segment on which wearable textile article 1 is being worn.

Preferably, each of first and second reinforcement bands 30, 31 follows a curved path having a preferred direction parallel to the direction of the generating lines of tubular element 2.

In addition, first reinforcement band 30 and/or second reinforcement band 31 is/are made of a fabric comprising a weave of weft threads and warp threads made of polymeric material, affording improved support to the muscles of the joint or body segment.

Preferably, the polymeric material used to make first and/or second fabric portion 200, 201 and/or first and/or second reinforcement band 30, 31 comprises a polyamide material. More preferably, the polymeric material used to make first and/or second fabric portion 200, 201 and/or first and/or second reinforcement band 30, 31 comprises a polyamide material and an elastomeric material.

According to an embodiment of wearable textile article 1, second fabric portion 201 comprises an opening 211 defined by an opening border 211'. This opening 211 is covered by an additional fabric portion 212 glued or fused in the vicinity of opening border 211'. This makes it possible to afford adequate flexibility in the vicinity of the rear portion of a joint, for instance, such as at the popliteal fossa or elbow fold. Preferably, additional fabric portion 212 is perforated to allow for improved breathing.

According to a preferred embodiment, first and second reinforcement bands 30, 31 extend substantially along the entire height H of the tubular element.

According to yet another embodiment variant, given a plane of symmetry Y that divides the tubular element into two half portions, first reinforcement band 30 is symmetrical to second reinforcement band 31 with respect to said plane of symmetry Y. In other words, a first path P along which first reinforcement band 30 lies, is symmetrical—with respect to plane of symmetry Y—to a second path P' along which second reinforcement band 31 lies.

Preferably, first reinforcement band 30 and second reinforcement band 31 extend continuously along a path P, P' that runs from a front area A of tubular element 2, intended to be placed in a front zone of a body segment when the textile article is being worn, to a rear area B of tubular element 2 intended to be placed in a rear zone of the body segment when the textile article is being worn.

In an embodiment variant, for example in the case of an arm brace, it is preferable for first reinforcement band 30 to sit exclusively on a front area A of tubular element 2, intended to be arranged in a front area of a body segment, and for second reinforcement band 31 to sit on a rear area B of tubular element 2, intended to be arranged in a rear area of the body segment when the textile article is being worn.

A particularly advantageous variant of wearable textile article 1, such as that shown in FIGS. 1 to 7, has tubular element 2 made solely of the joining together of said first fabric portion 200 and said second fabric portion 201. In other words, no additional portions of fabric are provided to form the tubular shape.

In another variant of the wearable textile article, such as that shown in FIGS. 8 to 15, tubular element 2 comprises at least a third fabric portion 202, which is also made of a fabric made from the weaving of weft threads and warp threads made of polymeric material (for example, polyamide or polyester or elastane and/or recycled fibers). In this variant, tubular element 2 comprises a third fusing area 302 and a fourth fusing area 303. First fabric portion 200 is fused to third fabric portion 202 (preferably by ultrasonic bonding or heat-sealing) along third fusing area 302 and along fourth fusing area 303. In addition, third fabric portion 202 comprises a left flap 202' and a right flap 202" placed side by side and fused together (preferably by ultrasonic bonding or heat-sealing) at least partially along this fourth fusing area 303. In this way, left flap 202', right flap 202", and first fabric portion 200 are joined together along fourth fusing area 303 so as to form the closed tubular shape.

In this embodiment variant, first reinforcement band 30 at least partially (or totally) also overlaps third fusing area 302 and second reinforcement band 31 at least partially (or totally) also overlaps fourth fusing area 303.

Preferably, first band 30 comprises a curved area 31' substantially in the shape of a "U" or "V" in such a way that when wearable textile article 1 is being worn on a thigh including the knee, said curved area 31' is arranged substantially around the kneecap, affording improved support for the kneecap as well as the entire knee joint.

As mentioned earlier, wearable textile article 1 according to the present invention is preferably a thigh brace having a height H such that, when the textile article is being worn, it surrounds both the thigh and the knee joint. Alternatively, the wearable textile article is preferably a sleeve for an upper limb, such as an elbow brace, having a height H such that, when the textile article is being worn, it surrounds both the arm or forearm and the elbow joint.

In the same way, the wearable textile article may be a calf brace or an ankle brace, wherein the tubular element has a height H such that, when the textile article is being worn, it surrounds the ankle joint and/or the calf.

The subject matter of the present invention is also a method for manufacturing the wearable textile article described in the preceding sections of this document. The method for manufacturing the wearable textile article comprises a series of steps, which will be more clearly understood in reference to FIGS. 4 to 7 and 11 to 15.

Figure 6:
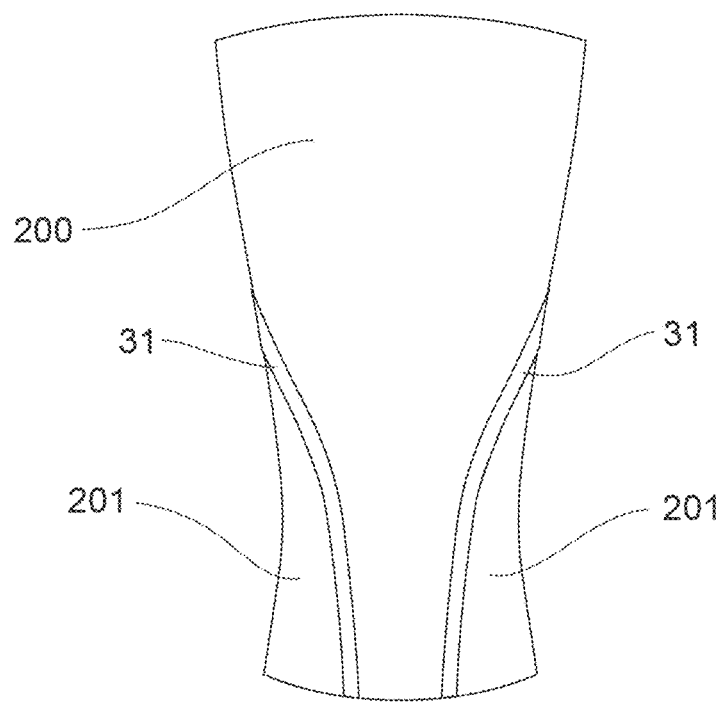
FIG. 6 shows another step in the method for making the article of the wearable textile article of FIG. 1, after the steps shown in FIGS. 4 and 5.
Figure 7:
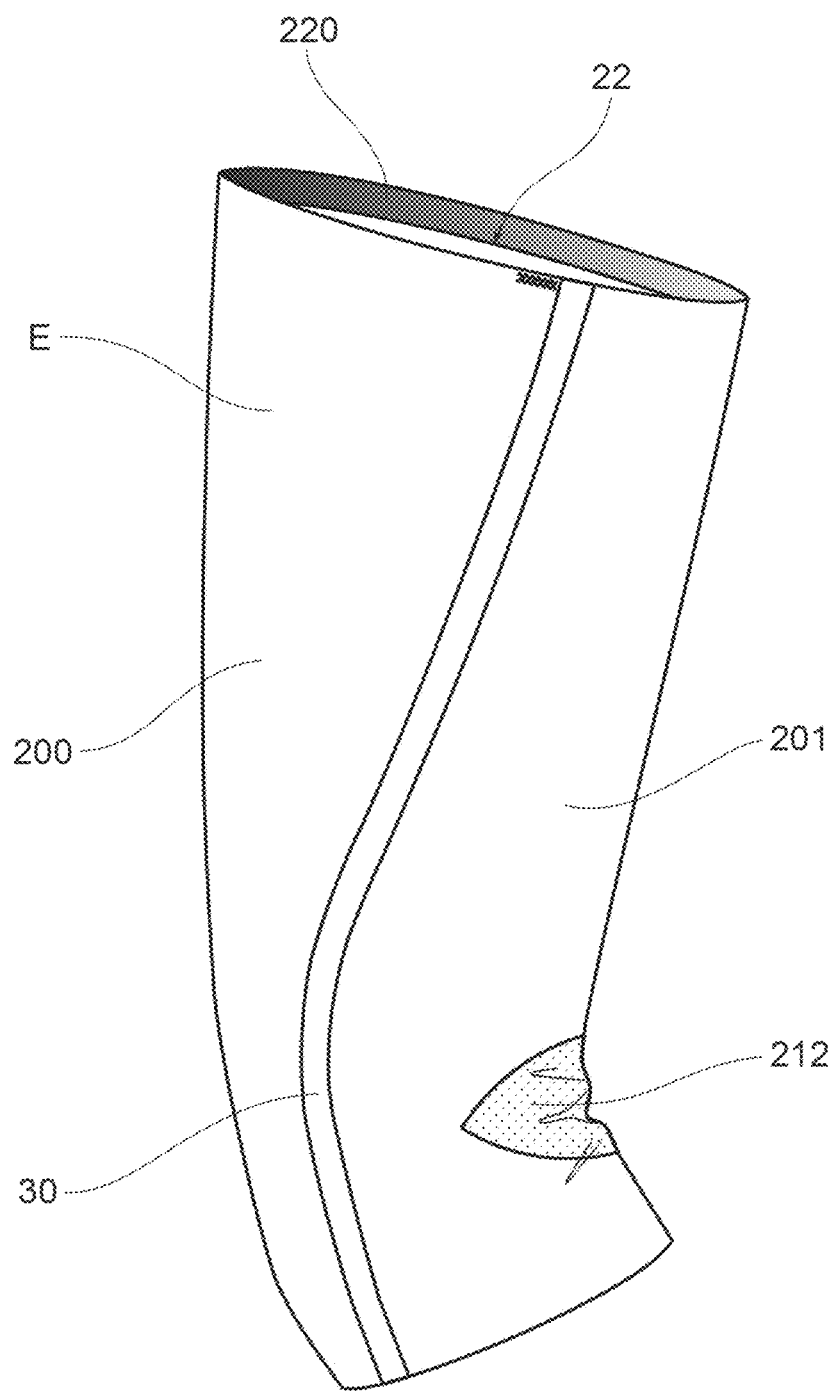
FIG. 7 shows a subsequent step in the method for making the article of the wearable textile article of FIG. 1, after the step shown in FIG. 6, in which an annular support band is applied.

The method for manufacturing a textile article comprises the steps of (preferably performed in the order given):
- a) providing first fabric portion 200 made of a fabric obtained by weaving weft threads and warp threads made of polymeric material;
- b) providing second fabric portion 201 made of a fabric obtained by weaving weft threads and warp threads made of polymeric material;
- c) fusing first fabric portion 200 to second fabric portion 201 along first fusing area 300 and second fusing area 301, preferably by ultrasonic bonding or heat-sealing, so as to obtain tubular element 2;
- d) joining first reinforcement band 30 in an at least partially overlapping way to first fusing area 300 on the external side E;
- e) applying second reinforcement band 31 in an at least partially overlapping way to second fusing area 301 on external side E. Upon completion of step e), for example, the tubular element shown in FIG. 6 is obtained.

Figure 4:
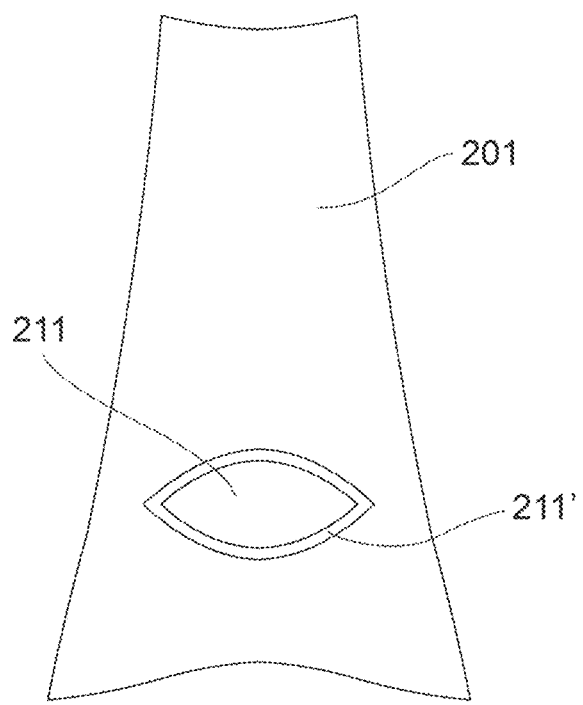
FIG. 4 shows the reverse side of a second fabric portion of a tubular element of the wearable textile article in the process of the making thereof in order to obtain the article of the wearable textile article of FIG. 1.
Figure 5:
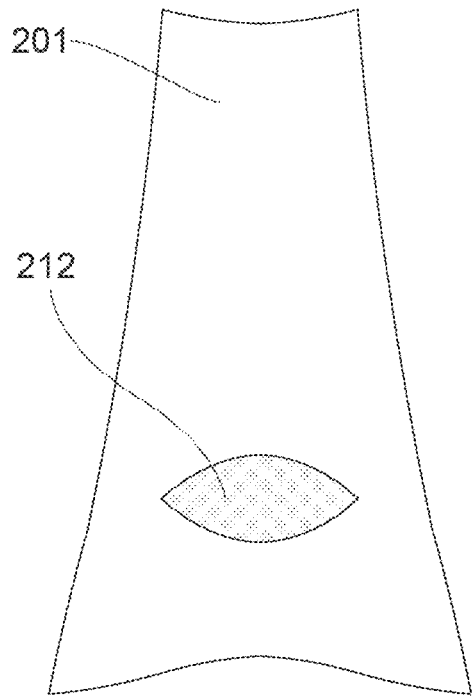
FIG. 5 shows the front side of the second fabric portion of FIG. 4.

Preferably, the method comprises the following steps before step c):
- providing an opening 211 made in second fabric portion 201 as shown, for example, in FIG. 4;
- on the reverse side of second fabric portion 201, gluing an additional fabric portion 212 at opening border 211' so as to cover opening 211 with said additional fabric portion 212 as shown, for example, in FIG. 5.

Subsequently, the method preferably comprises the step of applying an annular support band 220 at upper opening 22 on internal side I of textile article 1. Preferably, annular support band 220 is made of silicone material to ensure adequate adherence upon contact with skin.

In addition, the method preferably comprises the step of applying an annular accessory band 210 at lower opening 21 of tubular element 2 such as by fusing or gluing.

Figure 9:
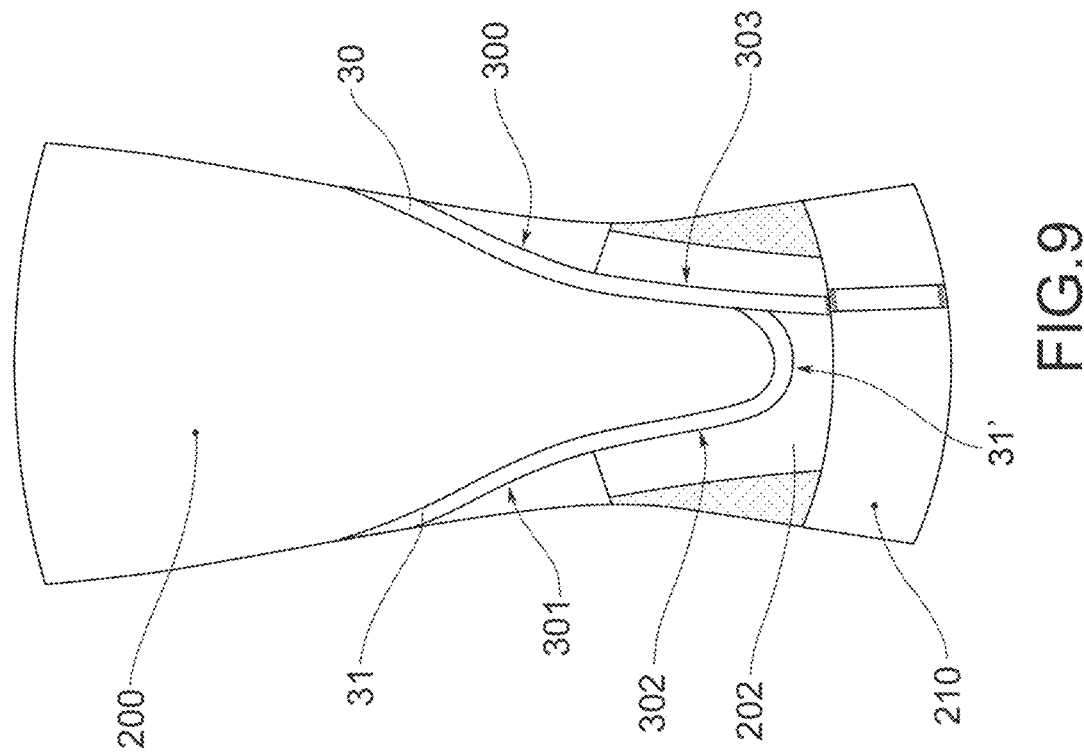
FIG. 9 shows a front view of the wearable textile article of FIG. 8.
Figure 11:
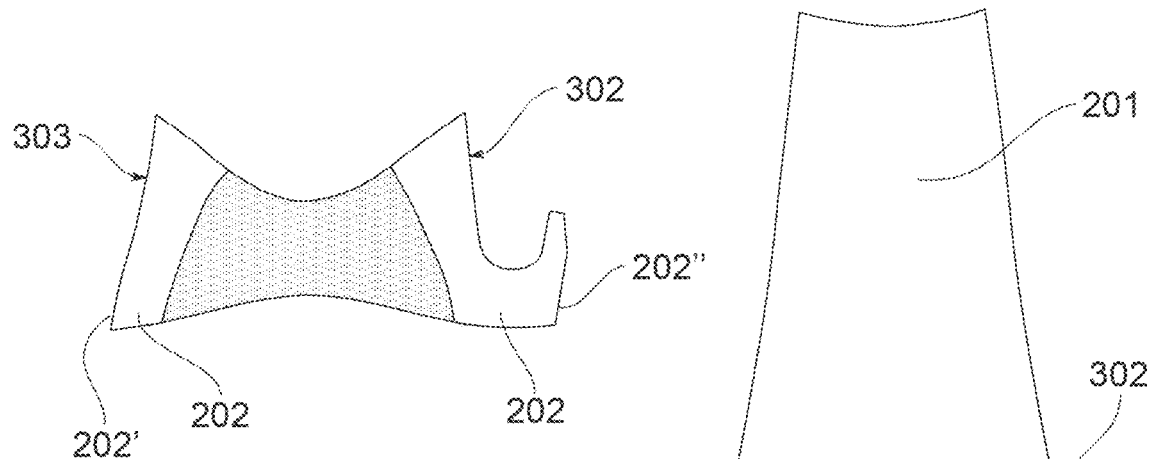
FIG. 11 shows a third fabric portion of a tubular element of the wearable textile article in a step in the making thereof to obtain the article of the wearable textile article of FIG. 8.
Figure 12:
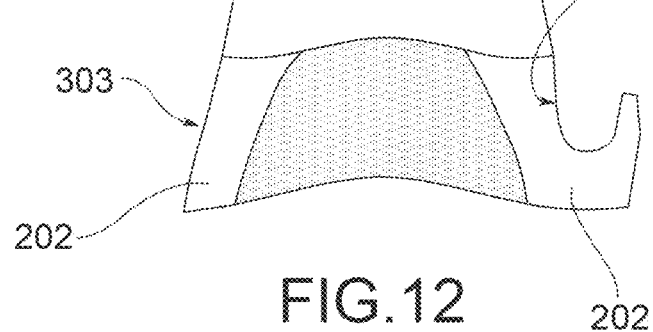
FIG. 12 shows a step in the method for making the article of the wearable textile article of FIG. 8 after the step shown in FIG. 11.
Figure 13:
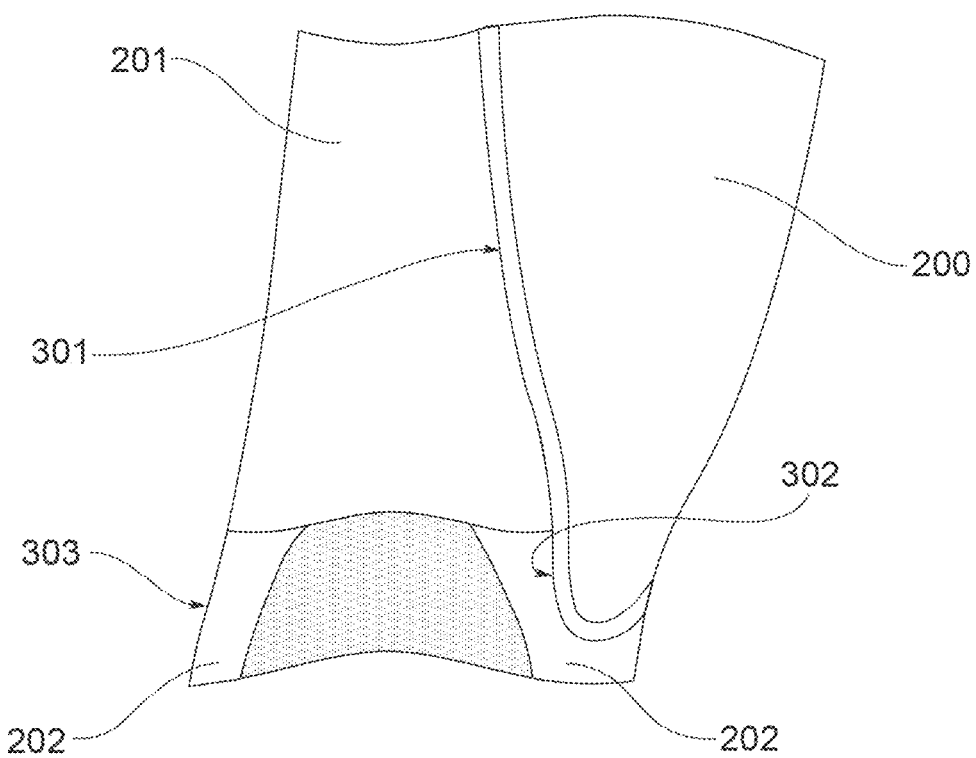
FIG. 13 shows another step in the method for making the article of the wearable textile article of FIG. 8 after the step shown in FIG. 12.
Figure 14:
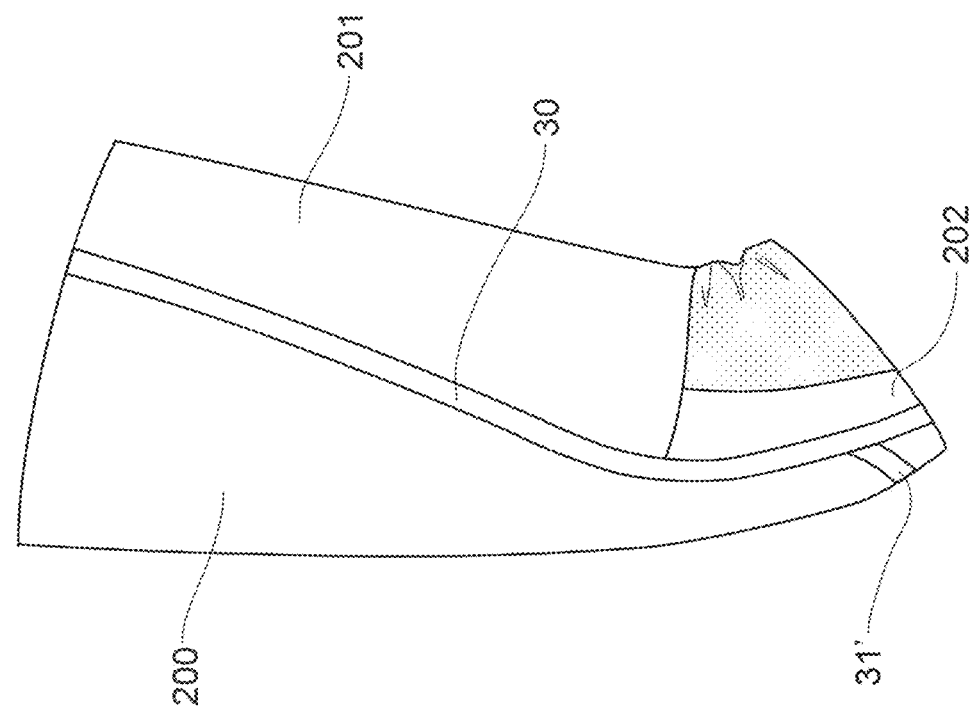
FIG. 14 shows another step in the method for making the article of the wearable textile article of FIG. 8 after the step shown in FIG. 13.

In reference to FIGS. 11 to 15 in particular, the method in this variant comprises the steps of:
- a1) providing first fabric portion 200 made of a fabric obtained by weaving weft threads and warp threads made of polymeric material;
- b1) providing second fabric portion 201 made of a fabric obtained by weaving weft threads and warp threads made of polymeric material;
- b2) providing third fabric portion 202 made of a fabric obtained by weaving weft threads and warp threads made of polymeric material;
- c1) at least partially overlapping second fabric portion 201 on third fabric portion 202 (as shown, for example, in FIG. 12);
- c2) fusing first fabric portion 200 to second fabric portion 201 and to third fabric portion 202 along second fusing area 301 and third fusing area 302, preferably by ultrasonic bonding or heat-sealing, as shown, for example, in FIG. 13;
- d1) joining second reinforcement band 31 in an at least partially (or totally) overlapping way to second fusing area 301 and third fusing area 302, on external side E (FIG. 13);
- d2) fusing first fabric portion 200 to second fabric portion 201 and to third fabric portion 202 along first fusing area 300 and fourth fusing area 303, preferably by ultrasonic bonding or heat-sealing, as shown, for example, in FIG. 14 and in FIG. 9;
- e1) applying first reinforcement band 30 in an at least partially (or totally) overlapping way to first fusing area 300 and to fourth fusing area 303, on external side E.

At the end of step e1) the tubular element shown in FIG. 14, for example, is obtained.

Figure 15:
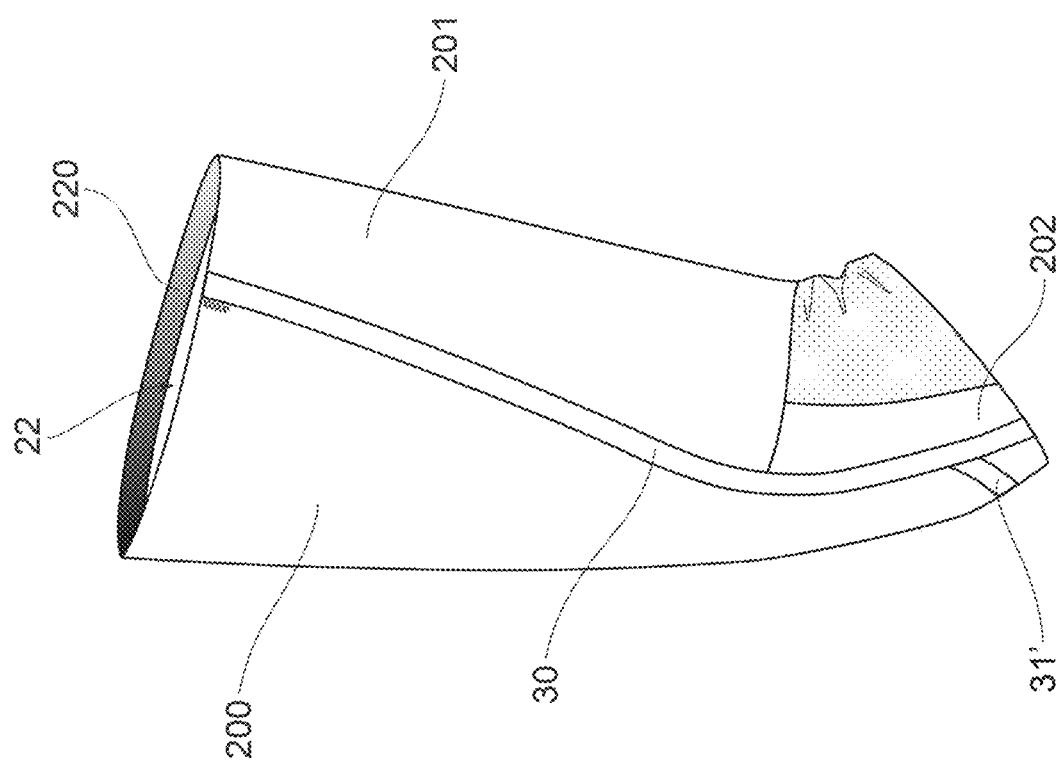
FIG. 15 shows another step in the method for making the wearable textile article of FIG. 8, after the step shown in FIG. 14, in which the annular support band is applied.

This variant of the method also preferably calls for applying an annular support band 220 to upper opening 22 on internal side I of textile article 1 (FIG. 15).

Figure 8:
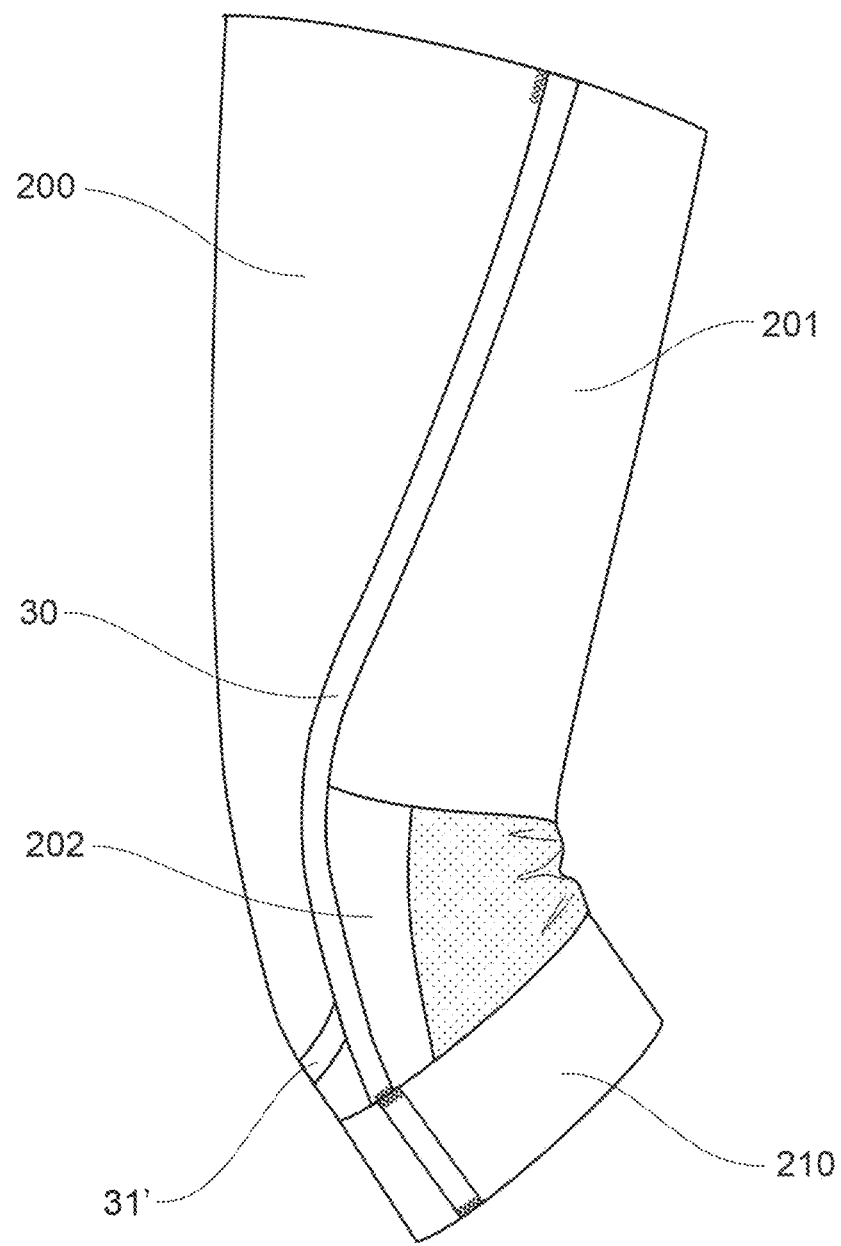
FIG. 8 shows a side view of the wearable textile article, according to one embodiment of the invention.
Figure 10:
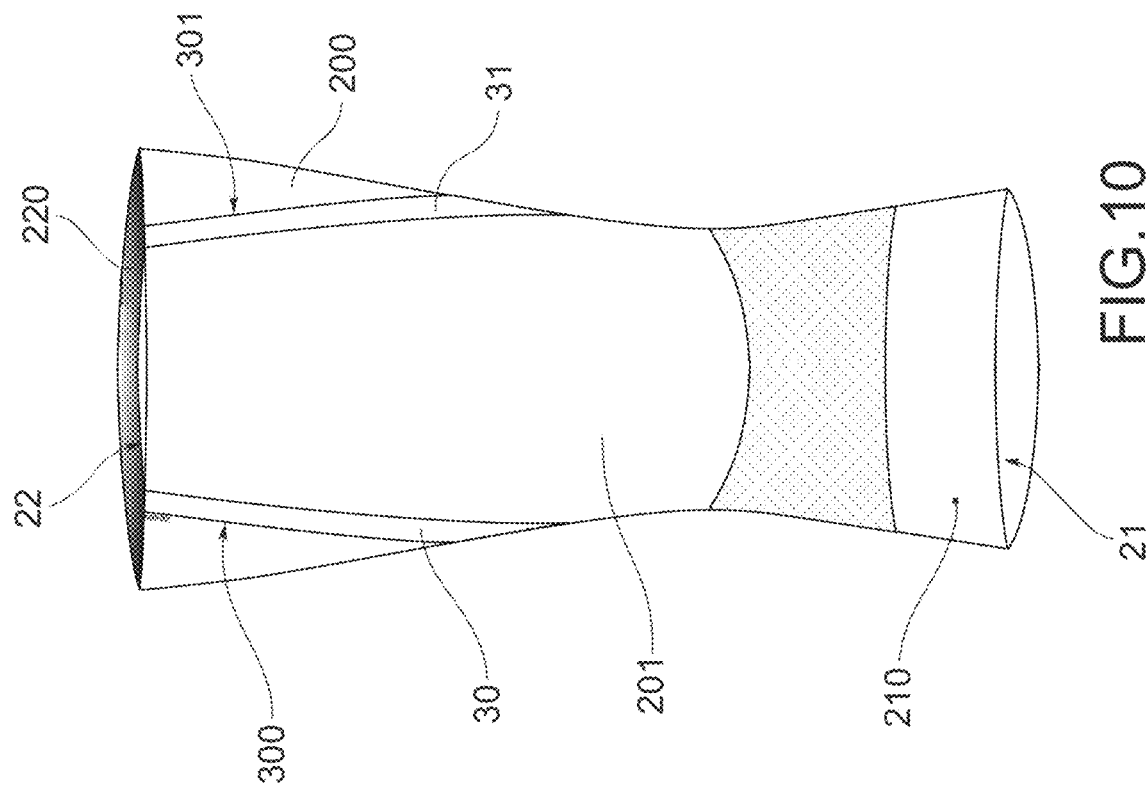
FIG. 10 shows a rear view of the wearable textile article of FIG. 8.

In addition, this variant of the method also preferably calls for applying, for example by gluing, an annular accessory band 210 at lower opening 21 of tubular element 2 (FIG. 8).

It is obvious that first fabric portion 200 and/or second fabric portion 201 and/or third fabric portion 202 is/are preferably flat fabric portions.

By way of innovation, the wearable textile article according to the present invention overcomes the drawbacks associated with the prior art. In particular, since the textile article is entirely made of portions of weft and warp fabric, effective and adequate support for muscle and joint function is achieved thanks to homogeneous compression in all directions (in both the axial and the circumferential directions). In addition, thanks to the weft and warp fabric, it is possible to achieve greater flexibility in terms of size and fit for the same amount of fabric used in the case of knitted tubular products of the prior art. In particular, items for adjusting compression, such as Velcro straps and similar items, are no longer necessary.

Furthermore, in a particularly advantageous way, tubular element 2 is totally free of stitching thanks to the fusing of fabric portions, thus ensuring maximum comfort for the wearer.

Even more advantageously, the presence of a first and a second reinforcement band further improves the muscle support function, creating an effect similar to the proprioceptive support effect of "taping" according to the prior art, but in this case directly incorporated into the wearable textile article. Advantageously, then, with a single action the user can put on the textile article, and the integral taping is positioned automatically to support muscle function without experiencing any application discomfort or annoyance due to stitching or bulky straps that do not remain in place.

Furthermore, thanks to the construction of the tubular element by means of fusing suitably-shaped flat fabric portions together, manufacturing of the wearable textile article is particularly simple and efficient. Indeed, no complicated knitting machines (or hosiery machines) are needed.

A person skilled in the art, for the purpose of satisfying specific requirements, could make modifications or substitutions of elements with other functionally equivalent ones to the embodiments of the wearable textile article and manufacturing method.

Such variants also fall within the scope of protection as defined by the following claims.

The invention claimed is:

1. A wearable textile article to support muscle function, comprising:
   a tubular element comprising a lower opening and an upper opening, an internal side configured for contact with a part of a human or animal body, and an external side opposite the internal side,
   wherein a first reinforcement band and a second reinforcement band are applied to said external side and/or to said internal side, each one of said first and second reinforcement bands being placed along a path that lies primarily along a direction extending from the lower opening to the upper opening,
   said tubular element further comprising a first fabric portion and a second fabric portion, said first fabric portion and second fabric portion each being made of a fabric obtained by weaving weft threads and warp threads of polymeric material, and a first fusing area and a second fusing area along which the first fabric portion is fused to the second fabric portion, so that the tubular element is completely free of stitching,
   wherein the first reinforcement band at least partially overlaps the first fusing area and the second reinforcement band at least partially overlaps the second fusing area, and
   wherein the second reinforcement band comprises a curved area having a U or V shape so that when the wearable textile article is being worn on a thigh up to and including a knee, said curved area is configured to sit around a kneecap;
   said tubular element further comprising a third fabric portion made of a fabric obtained by weaving weft threads and warp threads of polymeric material, and a third fusing area and a fourth fusing area along which the first fabric portion is fused to the third fabric portion;
   wherein the third fabric portion comprises a first flap and a second flap placed side by side and at least partially fused together along said fourth fusing area in such a way that the first flap is joined to the second flap and the first fabric portion along said fourth fusing area;
   wherein the first and second flaps are on opposing sides of the curved area of the second reinforcement band, and the curved area intersects the fourth fusing area.

2. The wearable textile article of claim 1, wherein the first flap is a left flap and the second flap is a right flap.

3. The wearable textile article of claim 2, wherein the first reinforcement band at least partially overlaps the third fusing area, and the second reinforcement band at least partially overlaps the fourth fusing area.

4. The wearable textile article of claim 1, wherein each of said first reinforcement band and second reinforcement band follows a curved path, with a portion of said curved path being parallel to a direction of longitudinal lines of the tubular element.

5. The wearable textile article of claim 1, wherein the first reinforcement band and/or the second reinforcement band is/are made of a fabric comprising a weave of weft threads and warp threads.

6. The wearable textile article of claim 1, wherein the polymeric material comprises a polyamide material.

7. The wearable textile article of claim 1, wherein each of said first reinforcement band and second reinforcement band extends continuously along a path that runs from a front area of the tubular element, configured to be placed in a front zone of a body segment when the wearable textile article is being worn, to a rear area of the tubular element configured to be placed in a rear zone of the body segment when the wearable textile article is being worn.

8. The wearable textile article of claim 1, said wearable textile article being a thigh brace having a height that, when the wearable textile article is being worn, the wearable textile article is configured to surrounds both the thigh and a knee joint.

9. The wearable textile article of claim 1, wherein the first fabric portion is fused to the second fabric portion by ultrasonic bonding.

10. The wearable textile article of claim 1, wherein a top of each of said first and second flaps abuts a bottom of said second fabric portion.

11. The wearable textile article of claim 1, further comprising an annular accessory band along a bottom edge of said third fabric portion.

12. The wearable textile article of claim 1, wherein the first reinforcement band extends past the curved area to a bottom of the third fabric portion.

13. A method for manufacturing a wearable textile article to support muscle function comprising:
   a tubular element comprising a lower opening and an upper opening, an internal side for contact with a part of a human or animal body, and an external side opposite the internal side,
   wherein a first reinforcement band and a second reinforcement band are applied to said external side and/or to said internal side, each one of said first and second reinforcement bands being placed along a path that lies primarily along a direction extending from the lower opening to the upper opening,
   said tubular element further comprising a first fabric portion and a second fabric portion, said first fabric portion and second fabric portion each being made of a fabric obtained by weaving weft threads and warp threads of polymeric material, and a first fusing area and a second fusing area along which the first fabric portion is fused to the second fabric portion, so that the tubular element is completely free of stitching,
   wherein the first reinforcement band at least partially overlaps the first fusing area and the second reinforcement band at least partially overlaps the second fusing area, and
   wherein the first second reinforcement band comprises a curved area having a U or V shape so that when the wearable textile article is being worn on a thigh up to and including a knee, said curved area sits around a kneecap,
   said tubular element further comprising a third fabric portion made of a fabric obtained by weaving weft threads and warp threads of polymeric material, and a third fusing area and a fourth fusing area along which the first fabric portion is fused to the third fabric portion,
   wherein the third fabric portion comprises a first flap and a second flap placed side by side and at least partially fused together along said fourth fusing area in such a way that the first flap is joined to the second flap and the first fabric portion along said fourth fusing area, wherein the first and second flaps are on opposing sides of the curved area of the second reinforcement band, and the curved area intersects the fourth fusing area, said method comprising:

a) providing the first fabric portion made of a fabric obtained by weaving weft threads and warp threads of polymeric material;
b) providing the second fabric portion made of a fabric obtained by weaving weft threads and warp threads of polymeric material;
c) fusing the first fabric portion to the second fabric portion along the first fusing area and the second fusing area to obtain the tubular element, so as to obtain a tubular shape completely free of stitching;
d) joining the first reinforcement band in an at least partially overlapping way to the first fusing area on the external side or the internal side; and
e) applying the second reinforcement band in an at least partially overlapping way to the second fusing area on the external side or the internal side.

* * * * *